US006770291B2

(12) United States Patent
Smyth-Templeton et al.

(10) Patent No.: US 6,770,291 B2
(45) Date of Patent: *Aug. 3, 2004

(54) LIPOSOME COMPLEXES FOR INCREASED SYSTEMIC DELIVERY

(75) Inventors: Nancy Smyth-Templeton, Houston, TX (US); George N. Pavlakis, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/991,028
(22) Filed: Nov. 20, 2001

(65) Prior Publication Data

US 2002/0122819 A1 Sep. 5, 2002

Related U.S. Application Data

(63) Continuation of application No. 09/242,190, filed as application No. PCT/US97/13599 on Aug. 1, 1997, now Pat. No. 6,413,544.
(60) Provisional application No. 60/024,931, filed on Aug. 30, 1996, now abandoned.

(51) Int. Cl.[7] .......................... A61K 9/127; A61K 9/133
(52) U.S. Cl. .......................... 424/450; 264/4.1; 264/4.3
(58) Field of Search ................... 264/4.1, 4.3; 424/450, 424/400, 1.21, 9.321, 9.51, 417; 428/402.2

(56) References Cited

U.S. PATENT DOCUMENTS 5,206,027 A * 4/1993 Kitaguchi
5,580,859 A * 12/1996 Felgner
5,827,703 A * 10/1998 Debs

FOREIGN PATENT DOCUMENTS

WO    WO 93/25673    12/1993
WO    93/25673    * 12/1993

OTHER PUBLICATIONS

Sternberg, J. of Liposome Research, 6 (3), pp. 515–533, 1966.*
Wasan, J. Pharm. Sciences, 85, (4), pp., 427–433, 1996.*
B. Sternberg, "Morphology of Cationic Liposome/DNA Complexes in Relation to Their Chemical Compositions", Journal of Liposome Research, 6(3), pp. 515–533 (1996).
T. Kato et al., "Synthetic Cationic Amphiphile for Lipsome-–Mediated DNA Transfection with Less Cytotoxicity" Biol. Pharm. Bull., 19(6), pp. 860–863 (1996).
E.K. Wasan et al., "Plasmid DNA is Protected Against Ultrasonic Cavitation–Induced Damage When Complexed to Cationic Liposomes", Journ. Pharm. Sciences, 85(4), pp. 427–433 (1996).

* cited by examiner

Primary Examiner—Gollamudi S. Kishore
(74) Attorney, Agent, or Firm—Edwards & Angell, LLP; Peter F. Corless, Esq.; Gregory B. Butler, Ph.D, Esq.

(57) ABSTRACT

Highly efficient cationic liposomes have been developed as an improved delivery system for biologically-active reagents. A novel structure, the sandwich liposome, is formed and comprises one or more biologically active agents internalized between two bilomellar liposomes. This structure protects the incoming agent and accounts for the high efficiency of in vivo delivery and for the broad tissue distribution of the sandwich liposome complexes.

These novel liposomes are also highly efficient carriers of nucleic acids. By using extruded DOTAP:cholesterol liposomes to form complexes with DNA encoding specific proteins, expression has been improved dramatically. Highest expression was achieved in the lung, while increased expression was detected in several organs and tissues.

7 Claims, 12 Drawing Sheets ly, the genetic material to be transferred should at least contain the gene to be transferred together with a promoter to control the expression of the new gene.

Methods for viral DNA delivery systems suffer from many inherent problems including immune responses, inability to deliver viral DNA vectors repeatedly, difficulty in generating high viral titers, and the possibility of infectious virus. Non-viral delivery methods provide an alternative system that is devoid of these problems. However, until now, low efficiency of DNA delivery by liposomes has limited the therapeutic application of this technology for gene therapy. The liposomes of the present invention have increased systemic DNA delivery and gene expression up to 150-fold over that previously reported.

LIPOSOME COMPLEXES FOR INCREASED SYSTEMIC DELIVERY

This is a continuation of application Ser. No 09/242,190, filed Oct. 4, 1999, now U.S. Pat. No. 6,413,544, which was a 35 U.S.C. 371 filing of PCT/US97/13599, filed Aug. 1, 1997, which claims priority to provisional application No. 60/024,931, filed Aug. 30, 1996, now abandoned.

FIELD OF THE INVENTION

The present invention is directed to a liposomal preparation which is based on a composition of specific lipids which form liposomes. It is also an object of the present invention to provide a method for preparing a liposomal composition carrying a biologically active agent. The liposomal delivery system of the present invention is used as highly efficient transfer and therapy methods.

BACKGROUND OF THE INVENTION

Lipidic particles may be complexed with virtually any biological material. This capability allows these complexes to be useful as delivery systems for proteins, therapeutic agents, chemotherapeutic agents and nucleic acids. Although lipidic complexes have been used for a myriad of drug therapies, one area where these delivery systems have shown promising results is in gene therapy. For gene therapy to be successful efficient and safe transfer of genes or biologically active reagent to a target cell is required. Hence the need for improved delivery systems, in both conventional and gene-based therapies is always at the forefront.

Lipidic particles have been shown to be efficient vehicles for many in vitro and in vivo applications. Lipidic particles complexed with DNA have been used in vitro (Felgner et al. (1987); Gao et al. (1991)) and in vivo (Nabel et al. (1990); Wang et al. (1987); Zhu et al. (1993); Soriano et al. (1983)) for the expression of a given gene through the use of plasmid vectors.

Formation of complexes of DNA with cationic lipidic particles has recently been the focus of research of many laboratories. Improved formulations of cationic lipids have greatly increased the efficiency of DNA delivery to cells in tissue culture (Felgner et al. (1987)). In contrast, intravenous DNA delivery in animals using cationic liposomes has been less efficient (Zhu et al. (1993); Philip et al. (1993); Solodin et al. (1995); Liu et al. (1995); Thierry et al. (1995); Tsukamoto et al. (1995); Aksentijevich et al. (1996)) limiting the therapeutic application of nonviral vectors to gene therapy. Improved liposome formulations for in vivo delivery is a valuable alternative to gene therapy using viral vectors and avoids several problems associated with viral delivery. Although efforts to synthesize new cationic lipids led to the discovery of more efficient transfection agents, their efficiency measured in tissue culture does not correlate with ability to deliver DNA after systemic administration in animals (Solodin et al. (1995)). Functional properties defined using in vitro experiments do not assess stability of the complexes in plasma or their pharmacokinetics and biodistribution, all of which are essential for in vivo activity (Felgner et al. (1994)). Colloidal properties of the complexes in addition to the physicochemical properties of their component lipids may determine these parameters.

The liposome provides an alternative to viral delivery systems in gene therapy which may involve the transfer of normal, functional genetic material into cells to correct an abnormality due to a defective or deficient gene product. Typically, the genetic material to be transferred should at Therefore, an object of the present invention is the synthesis of a highly efficacious liposome structure capable of delivering biologically active agents into a subject.

Another object of the present invention is the use of these stable liposomes as carriers of nucleic acids for delivery and expression of the nucleic acid product at a target site within an animal.

Yet another object of the present invention is the use of these stable liposomes as carriers of nucleic acids for delivery and expression of the nucleic acid product systemically to a patient.

A further object of the present invention is the production of kits containing the stable liposomes of the present invention, capable of carrying any nucleic acid of interest.

Another object of the present invention is to use liposomes carrying specific reagents for human gene therapy in treatment of disease.

Yet a further object of the present invention relates to providing a method for long-term expression of a gene product from a non-integrated nucleic acid in a patient.

SUMMARY OF THE INVENTION

The present invention relates to a novel liposome structure capable of carrying biologically-active reagents. These liposome structures are highly efficient vehicles for delivery of biologically active agents to target locations in a patient as well as provide systemic reagent delivery. The liposome complexes of the present invention are small in size and have a net +/− charge ("ρ") of about 2.

The present invention further relates to a method of preparing these novel liposomes comprising the steps of heating, sonicating, and extrusion of the liposome structures. The method of preparation of the present invention produces complexes of appropriate and uniform size, which are structurally stable and produce maximal extrusion. Liposomes prepared by this method are also encompassed by the present invention.

The present invention further relates to a novel liposome structure capable of carrying nucleic acids. The present invention also relates to an improved liposome formulation comprising DOTAP (1,2-bis(oleoyloxy)-3-(trimethylammonio)-propane) and cholesterol ("Chol") and a nucleic acid which produces exceptionally high gene expression and protein production in vivo. These formulations are extremely stable, homogeneous in size, and can complex nucleic acids over a wide range of nucleic acid:liposome ratios. The present invention demonstrates up to 150-fold greater gene expression following in vivo systemic delivery in animals as compared to formulations previously described in the literature.

The present invention also relates to liposomes carrying non-immunogenic targeting ligands and stealth lipids. These ligands facilitate the targeted delivery of the liposomes to a particular tissue or site in the body.

The present invention relates to kits containing the present liposome structure capable of carrying a reagent within it. One such kit may comprise the liposome structures ready for the user to add the biological reagent of interest. A kit may further comprise a liposome preparation and one or more specific biologically-active reagents for addition to the liposome structure. Another kit of the present invention comprises a set of liposome structures, each containing a specific, biologically-active reagent, which when administered together or sequentially, are particularly suited for the treatment of a particular disease or condition.

The present invention provides a therapeutic method of treating diseases, ailments and conditions based upon a liposome-facilitated delivery of biologically active agents. For example, the present invention provides a pharmaceutical liposomal formulation for the delivery of nucleic acids using systemic administration to provide long-term expression of a given nucleic acid. In addition, the present invention encompasses in vitro cell transfection followed by tissue transplantation such that the transfected cells may be incorporated in transplanted tissue. This method is referred to as in vitro/ex vivo transfer. Other biologically-active agents may be encapsulated in the liposomes of the present invention for in vitro/ex vivo methods so long as a +/− charge of positive 2 is maintained.

The present invention further provides an effective vaccine vehicle capable of effective delivery, boosting antigen-immune response and lowering unwanted extraneous immune response, presently experienced with adjuvants.

DETAILED DESCRIPTION OF THE INVENTION

Figure 1A:
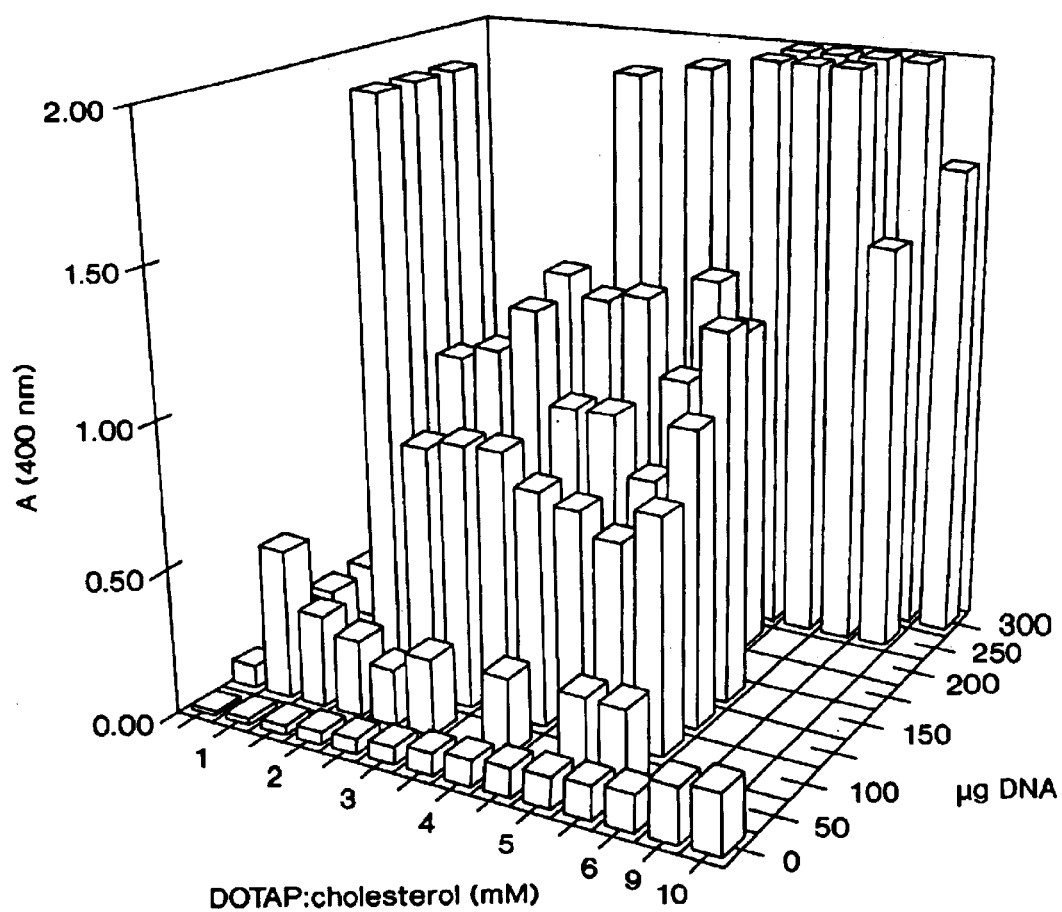
FIG. 1A. Phase Diagram for DOTAP:Chol-DNA liposome complexes. Liposomes were prepared (see Example 1) and complexed with DNA (see Example 2) at various concentrations of DNA and liposomes in a final volume of 200 μl. The absorbance at 400 nm was determined for 1:20 dilutions of each DNA:liposome complex and plotted. An absorbance of 2.0 indicates precipitation of the complexes. White boxes indicate data points not determined.

The present invention relates to the discovery that liposomes of a specific composition forming a stable structure are efficient carriers of biologically active agents. The liposome containing one or more biologically active agents may then be administered into a mammalian host to effectively deliver its contents to a target cell. The liposomes of the present invention are small and carry a net +/− charge (referred to herein as "ρ") of about 2 when complexed with a biologically active agent. The liposomes are capable of carrying biologically active agents, such that the agents are completely sequestered. The liposomes comprise a cationic lipid, DOTAP and cholesterol or a cholesterol derivative. Preferably, at least one biologically active agent to be complexed with the liposome is negatively charged. Additional biologically active agents may be complexed with the liposome regardless of their charge, so long as ρ is maintained in the range of 1 to 3, preferably about 2. The liposome-biologically active agent complex of the present invention forms an invaginated structure referred to herein as a "sandwich liposome," because the biologically active agents are sandwiched (and thus sequestered) between the lipid bilayers.

The present invention also provides a targeting means, such that the liposomes can be delivered to specific target sites. The targeting means comprises decorating the outside of the sandwich liposome complexes with one or more ligands specific for a particular target site or sites.

"Biologically active agents" as the term is used herein refers to molecules which affect a biological system. These include molecules such as proteins, nucleic acids, therapeutic agents, vitamins and their derivatives, viral fractions, lipopolysaccharides, bacterial fractions and hormones. Other agents of particular interest are chemotherapeutic agents, which are used in the treatment and management of cancer patients. Such molecules are generally characterized as antiproliferative agents, cytotoxic agents and immunosuppressive agents and include molecules such as taxol, doxorubicin, daunorubicin, vinca-alkaloids, actinomycin and etoposide.

The term "nucleic acids" means any double strand or single strand deoxyribonucleic acid (DNA) or ribonucleic acid (RNA) of variable length. Nucleic acids include sense and anti-sense strands. Nucleic acid analogs such as phosphorothioates, phosphoramidates, phosphonates analogs are also considered nucleic acids as that term is used herein. Nucleic acids also include chromosomes and chromosomal fragments. Potential genes include but are not limited to: immune system proteins HLA-B7 and IL-2, cystic fibrosis transmembrane conductance regulator, Factor VIII, Factor IX, insulin and erythropoietin. (Felgner (1997)).

Antisense oligonucleotides may potentially be designed to specifically target genes and consequently inhibit their expression. In addition this delivery system may be a suitable carrier for other gene-targeting oligonucleotides such as ribozymes, triple helix forming oligonucleotides or oligonucleotides exhibiting non-sequence specific binding to particular proteins or other intracellular molecules. For example, the genes of interest may include retroviral or viral genes, drug resistance genes, oncogenes, genes involved in the inflammatory response, cellular adhesion genes, hormone genes, abnormally overexpressed genes involved in gene regulation.

One embodiment of the present invention comprises encapsulating a nucleic acid within a liposome and expressing a gene encoded on the nucleic acid within the target host cell, through the use of plasmid DNA. Conversely, the expression of a gene may be inhibited, for example, through the use of antisense oligonucleotides. Alternatively, a chemotherapeutic agent may act as the biologically active agent and be encapsulated within a liposome, thereby sequestering its toxic effects from non-targeted tissues.

The present invention may utilize more than one nucleic acid or biologically active agent in the liposome of the present invention. For example, proteins such as DNA binding proteins can be added as additional biologically active agents to DNA-sandwich liposomes to facilitate a therapeutic effect. Another example includes sandwich liposomes carrying genes for anti-cancer treatment which are also carrying anti-cancer chemotherapeutic agents. This approach is especially attractive when targeted liposomes are used to deliver both gene therapy and chemotherapy specifically to cancer cells.

"Liposome" as the term is used herein refers to a closed structure comprising of an outer lipid bi- or multi-layer membrane surrounding an internal aqueous space. In particular, the liposomes of the present invention form vase-like structures which invaginate their contents between lipid bilayers (see FIG. 4). Liposomes can be used to package any biologically active agent for delivery to cells. In one example, DNA can be packaged into liposomes even in the case of plasmids or viral vectors of large size which may be maintained in a soluble form. Such invaginated liposome:DNA complexes are ideally suited for direct application to in vivo systems. These liposomes entrap compounds varying in polarity and solubility in water and other solvents.

By "nucleic-acid-sandwich" liposomes is meant, the layered composition comprising a structure having lipid bilayers with nucleic acid molecules inserted between and protected by the lipid layers.

One embodiment of the present invention relates to an improved liposome formulation comprising a nucleic acid, DOTAP and cholesterol which produces exceptionally high gene expression and protein production in vivo. In addition, these formulations are extremely stable, homogeneous in size, and can complex nucleic acids over a wide range of nucleic acid:liposome ratios. This flexibility allows optimization of the complexes for delivery in vivo. Most tissues other than lung are extremely sensitive to the nucleic acid:liposome ratio. In addition, the stability of DOTAP:Chol liposomes at high concentrations of liposome and DNA allows for increased concentrations of DNA for delivery and expression.

The present invention further relates to a method of preparing these novel liposomes comprising the steps of heating, sonicating, and sequential extrusion of the lipids through filters of decreasing pore size, thereby resulting in the formation of small, stable liposome structures. The method of preparation of the present invention produces complexes of appropriate and uniform size, which are structurally stable and produce maximal extrusion.

Liposomes comprising DOTAP and at least one cholesterol and/or cholesterol-derivative, present in a molar ratio range of 2.0 mM–10 mM provide an effective drug delivery system. More preferably, the molar ratio of DOTAP to cholesterol is 1:1–3:1. The liposomal composition of the present invention has shown to be very stable in a biological environment.

Cholesterol derivatives may be readily substituted for the cholesterol element of the present liposome invention. Many cholesterol derivatives are known to the skilled artisan. Examples include but are not limited to cholesteryl acetate and cholesteryl oleate.

Many DNA preparation protocols are available to the skilled artisan; any of which can be employed to prepare DNA for use in the liposomes of the present invention. Three DNA preparation protocols are preferred, namely, alkaline lysis followed by PEG precipitation, anion-exchange chromatography (Qiagen), and a modified alkaline lysis protocol (see Example 3). The modified alkaline lysis protocol is a particularly preferred method to obtain high DNA yield, have low levels of endotoxin, and achieve high levels of gene expression.

Transfer Therapy Methods

The liposomal composition of the present invention may be administered into patients parenterally in order to achieve transfer therapy of one negatively-charged, biologically-active agent along with other biologically active agents. Moreover, this technique may be used for "ex vivo" transfer therapy where tissue or cells are removed from patients, then treated and finally reimplanted in the patient (U.S. Pat. No. 5,399,346, describing the details of ex vivo human gene therapy is incorporated herein by reference). Alternatively, systemic therapy is also effective in administering the liposome of the present invention.

Many diseases can be treated via the drug delivery system of the present invention. Diseases such as diabetes, atherosclerosis, chemotherapy-induced multi-drug resistance, and generally, immunological, neurological (Ho and Sapolsky (1997)) and viral diseases (Friedmann (1997)) can be treated using the present drug delivery system.

Non-limiting examples of gene therapy approaches for treating cancer which can employ the delivery system of the present invention include: antisense therapy (to block synthesis of proteins encoded by deleterious genes), chemoprotection (to add proteins to normal cells to protect them from chemotherapies), immunotherapy (to enhance the body's immune defenses against cancer), pro-drug or suicide gene therapy (to render cancer cells highly sensitive to selected drugs), tumor suppressor genes (to replace a lost or damaged cancer-blocking gene), antibody genes (to interfere with the activity of cancer-related proteins in tumor cells) and oncogene down-regulation (to shut off genes that favor uncontrolled growth and spread of tumor cells) (Blaese (1997)).

The delivery system of the present invention is also useful for correcting the ion transport defect in cystic fibrosis patients by inserting the human CFTR (cystic fibrosis transmembrane conductance regulator) gene. Oral administration such as nebulization may be particularly suitable. In addition, the liposomes of the present invention can be used for the inhibition of tumor cells by administering in tumor cells a molecule inhibiting tumorigenesis or a gene coding for an antisense polynucleotide directed to mRNA transcripts of angiogenic factors. In addition, ribozymes may be encapsulated and enzymatically attack specific cellular contents.

The liposomes of the present invention containing the nucleic acid drug can be administered by intravenous, intramuscular, intraperitoneal, subcutaneous intra-lesional, oral or aerosol means. (Stribling et al. (1992)).

For aerosol administration, a patient receives one or more nasal or bronchial aerosol administrations of the liposome complex. The dosages will vary based upon age, body composition and severity of disease or condition. (Caplen et al. (1995)).

Other routes of administration will be known to the skilled artisan and can be readily used to administer the liposomes of the present invention. Examples include but are not limited to mucosal, intra-uteral, intradermal and dermal.

A proposed daily dosage of active compound for the treatment of humans is 0.1 $\mu$g DNA/kg to 5.0 mg DNA/kg, which may be conveniently administered in 1–10 doses. The actual dosage amount administered can be determined by physical and physiological factors such as body weight, severity of condition, idiopathy of the patient and on the route of administration. With these considerations in mind, the dosage of DNA-liposome complex for a particular subject and/or course of treatment can readily be determined.

The liposome of the invention may be formulated for parenteral administration by bolus injection or continuous infusion. Formulation for injection may be presented in unit dosage form in ampoules, or in multi-dose containers with an added preservative. The compositions may take such forms as suspension, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile pyrogen-free water, before use.

The liposomes according to the invention may be formulated for administration in any convenient way. The invention therefore includes within its scope pharmaceutical compositions comprising at least one liposomal compound formulated for use in human or veterinary medicine. Such compositions may be presented for use with physiologically acceptable carriers or excipients, optionally with supplementary medicinal agents. Conventional carriers can also be used with the present invention.

For oral administration, the pharmaceutical composition may take the form of, for example, tablets, capsules, powders, solutions, syrups or suspensions prepared by conventional means with acceptable excipients.

An improved method for preparing the liposomes of the present invention employs sonication, heating, and extrusion (see Example 1 for detailed description). Generally, the method requires that the lipid components be mixed in the appropriate concentrations, dissolved in an organic solvent, such as chloroform or the like, evaporated into a thin film and lyophilized. The film is then rehydrated in an aqueous solution and mixed for a period at 35°–60° C. Thereafter, the mixture is sonicated and heated to a temperature between 40° C.–60° C. This mixture is then sequentially extruded through filters of decreasing size. Sonicated liposomes are preferably extruded through filters of decreasing pore sizes, including 0.1 μm, by using sufficient heating.

Various nucleic acids may be added to these liposomes in a wide range of concentrations. Nucleic acids are preferably added to the liposomes at a concentration of 50–300 μg per dose. These concentrations vary widely depending upon the ratio of DOTAP:Chol in the particular liposome preparation. For example, if a liposome having a molar ratio of DOTAP:Chol of about 1:1 is used, then a preferred concentration of nucleic acid is between 80–175 μg per dose.

Extruded DOTAP:Chol liposomes prepared by the method of the present invention were compared to non-extruded DOTAP:Chol liposomes (multilamellar vesicles, MLVs) prepared by the conventional method. (Liu et al. (1997)). The extruded liposomes form sandwich liposomes whereas the non-extruded liposomes do not form such structures. Protein expression from nucleic acid: sandwich liposomes was approximately 2-fold higher as compared to MLVs. Furthermore, MLVs containing 5 mM to 10 mM DOTAP:Chol have increased toxicity when delivered systemically.

Production of chloramphenicol acetyl transferase ("CAT") is the most widely used method to measure protein expression and is a well recognized model protein expression system. (Wheeler et al. (1996); Lee et al. (1996); Felgner (1996)). In one embodiment of the present invention the sandwich liposome complexes (i.e. FIGS. 2A, D, E) produced 100-fold greater amounts of CAT in the lung compared to CAT produced using DOTIM:Chol SUVs. (Solodin et al. (1995)). Those skilled in the art will readily recognize that any nucleic acid can be used in the present invention.

By using sandwich liposomes for systemic nucleic acid delivery, a broad biodistribution is produced (i.e. FIG. 2B) that is greater than that produced by any other cationic liposome formulation reported. (Zhu et al. (1993); Philip et al. (1993); Solodin et al. (1995); Liu et al. (1995); Thierry et al. (1995); Tsukamoto et al. (1995); Aksentijevich et al. (1996); Wheeler et al. (1996); Liu et al. (1997); Hong et al. (1997); Lee et al. (1996); Felgner (1996)).

Targeted Delivery

Because the biologically active agent is sequestered in the sandwich liposomes, targeted delivery is achieved by the addition of peptides and other ligands without compromising the ability of these liposomes to bind and deliver large amounts of the agent. The ligands are added to the liposomes in a simple and novel method. First, the lipids are mixed with the biologically active agent of interest. Then ligands are added directly to the sandwich-liposomes to decorate their exterior surface. The stability and net positive charge of the liposomes allow ligands to be directly added to their exterior.

The sandwich liposome complexes of the present invention may be used to make effective artificial viruses. Because the outside of the sandwich liposome complexes is substantially free of biologically active agents, targeting ligands may be placed on the outside after sandwich liposome formation, without compromising the effect of the targeting ligand or the ability of the biologically active agents to be delivered and expressed. This may enable delivery to specific organs and tissues. The size of the sandwich liposome complexes responsible for efficient delivery, 200 to 450 nm (see also Table 1), is preferred for the addition of targeting ligands. Our experiments demonstrate the usefulness of this approach (See Example 9, FIG. 7).

Many ligands may be employed for this targeting step of liposome preparation, depending upon the site targeted for liposome delivery. For example, lactosyl ceramide, and peptides that target the LDL receptor related proteins, such as apolipoprotein E3 ("Apo E") has been useful in targeting the liposomes of the present invention to the liver. In particular, the use of the Apo E ligand resulted in a 4-fold greater gene expression in the liver.

In addition, magnetic resonance imaging shows that the half-life of sandwich liposome complexes is at least 5 hours in circulation. This demonstrates that the sandwich liposomes have time to reach the intended target intact.

Alternatively, monoclonal antibody fragments may be used to target delivery to specific organs in the animal including brain, heart, lungs or liver.

The present method to add ligands only to the outer surface after complex formation is unique and has the advantage of avoiding disruption of the biologically active agent liposome complex formation due to steric or ionic interactions with the targeting ligand.

Figure 3A:
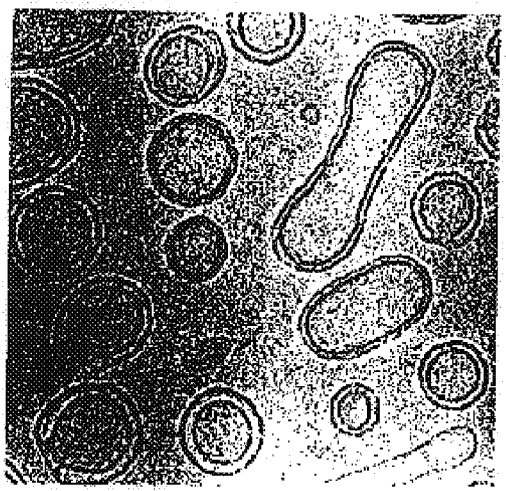
FIG. 3. Cryoelectron micrographs of liposomes and DNA:liposome complexes. (A) 5 mM DOTAP:Chol liposomes. A thin film was prepared by dipping and withdrawing a 700 mesh copper grid (3 mm diameter, 3 to 4 μm thick) in the DOTAP:Chol suspension. After blotting away excess liquid, the thin films that form between the bars of the grid were vitrified in melting ethane. After cryotransfer, the specimen was observed at −170° C. in a Philips CM 12 microscope at low dose, 120 kV (Frederik et al. (1991)). Note the continuity between concentric bilayers in some of the vesicles, giving the shape of a vase with an orifice. (B) 5 mM DOTAP:Chol liposomes mixed with 150 μg DNA/ 200 μl. These structures are referred to as DNA-sandwich liposomes. A thin vitrified specimen was prepared from this DNA:liposome suspension and observed at −170° C. (as in A). Note the packing of DNA (electron opaque addition to the lipid) in the interior of the vesicles. Lipid-DNA interaction has apparently resulted in remodeling of the vesicles and changed the accessibility of DNA. (C) Enlarged image of a DOTAP:Chol vase. (D) Enlarged image of DNA packed between two DOTAP:Chol vases. (E) 5 mM DOTAP:DOPE liposomes. (F) 5 mM DOTAP:DOPE liposomes mixed with 150 μg of DNA in a 200 μl final volume.
Figure 3B:
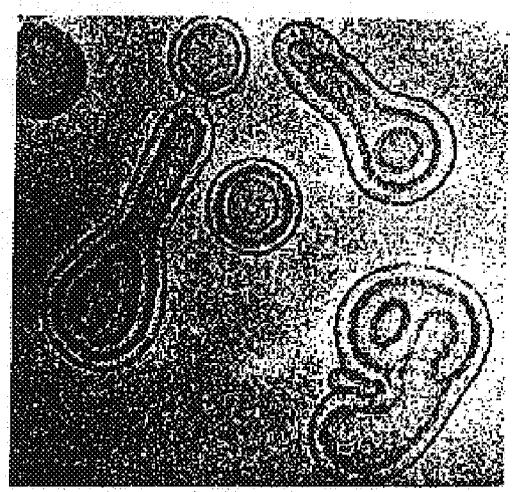
Figure 3C:
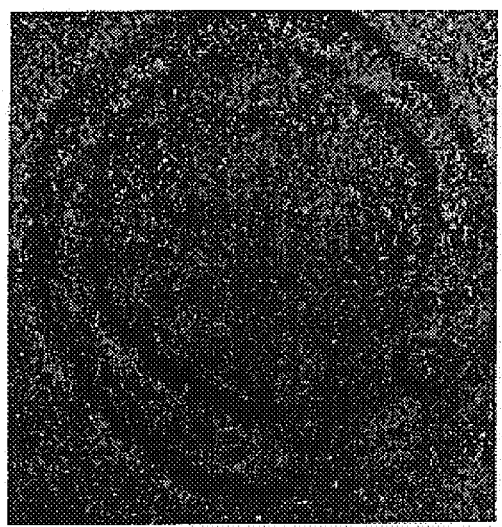

One embodiment of the liposomes of the present invention are completely invaginated with two concentric lamellae and a small orifice with an approximate diameter of 50 nm (FIG. 3A), which are called a "vase structure" (FIG. 3C). For example, of 536 vesicles observed, 88% were invaginated structures, and only 12% were the typical small unilamellar vesicles (SUVs). The invaginated sandwich liposomes of the present invention include other structures, such as, bilamellar vases, bilamellar and unilamellar tubular shapes, unilamellar erythrocyte shapes, and unilamellar bean shapes.

Liposomes are examined after each step in the process of making the sandwich liposomes and unilamellar spheres are observed until extrusion through the 0.1 μm filter. This extrusion step produces invaginated structures with excess surface area. Performing only mild sonication (see Example 1) prior to extrusion is also recommended because high frequency sonication of DOTAP:Chol liposomes produces only SUVs and micelles. The bulk (88%) of sandwich liposomes prepared by the instant method are bilamellar and unilamellar invaginated vesicles.

Figure 4:
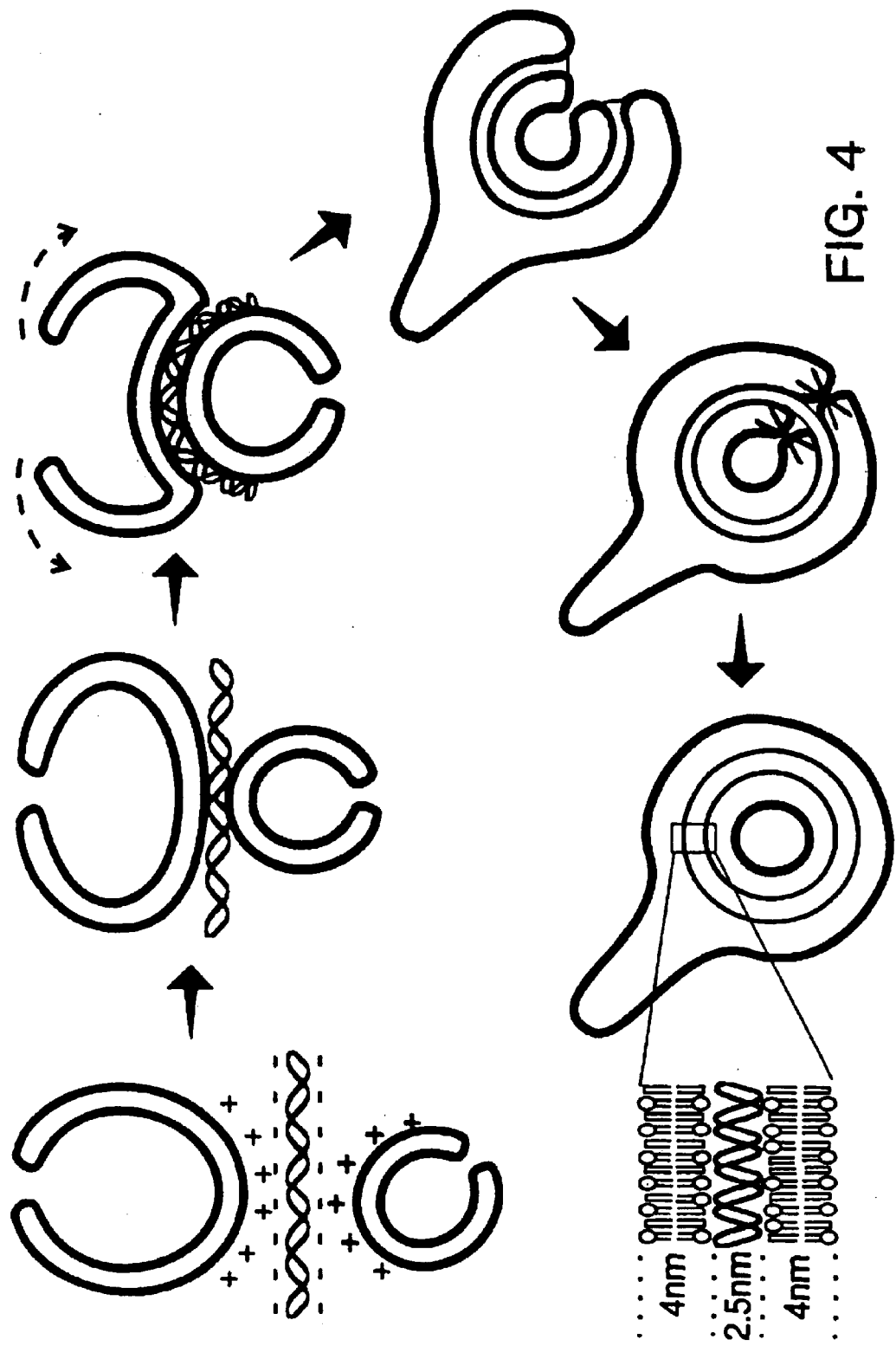
FIG. 4. Proposed model showing cross-sections of DOTAP:Chol liposomes interacting with supercoiled plasmid DNA. The X indicates fusion of lipid bilayers. The enlarged area shows proposed arrangement of DNA condensed between two 4 nm bilayers of DOTAP:Chol.
Figure 5:
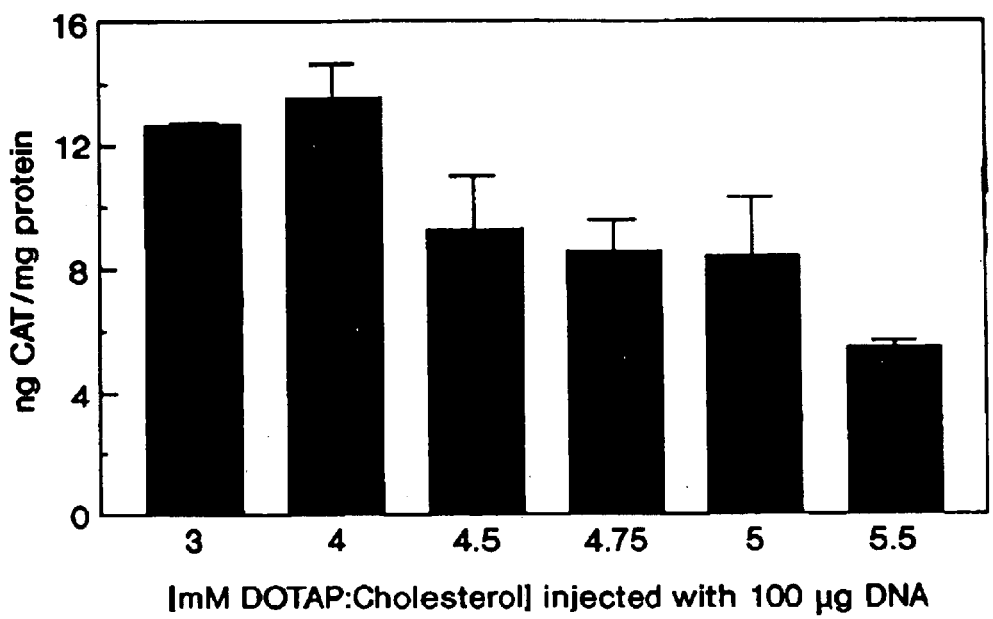
FIG. 5. Production of CAT in the mouse lung following systemic delivery using a variety of DOTAP:Chol concentrations complexed to 100 kg of DNA per tail vein injection. Concentrations of DOTAP:Chol used varied from 3.0 mM to 5.5 mM. The results showed slightly greater CAT protein production in the lung using 3.0 mM and 4.0 mM liposomes complexed to 100 μg DNA per tail vein injection than the amount of CAT produced using 5.0 mM liposome complexed to 150 μg DNA. In addition, a dose response was produced in vivo following injection of different concentrations of DOTAP:Chol used to make the DNA:liposome complexes.

It appears that the biologically active agent adsorbs onto the invaginated and tubular liposomes via electrostatic interactions (FIG. 4). Attraction of a second liposome to this complex results in further charge neutralization. If the liposomes are of unequal size, expanding electrostatic interactions with the biologically active agent cause inversion of the larger liposome and total engulfment of the biologically active agent. These structures are sandwich liposomes. Inversion can occur in these liposomes because of their excess surface area, which allows them to accommodate the stress created by the lipid interactions with the biologically active agent.

Figure 3D:
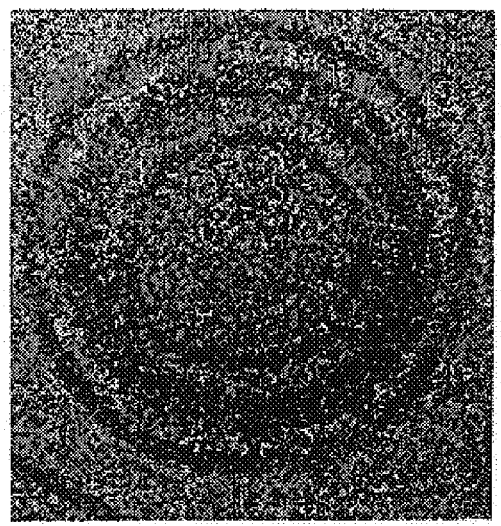
Figure 8:
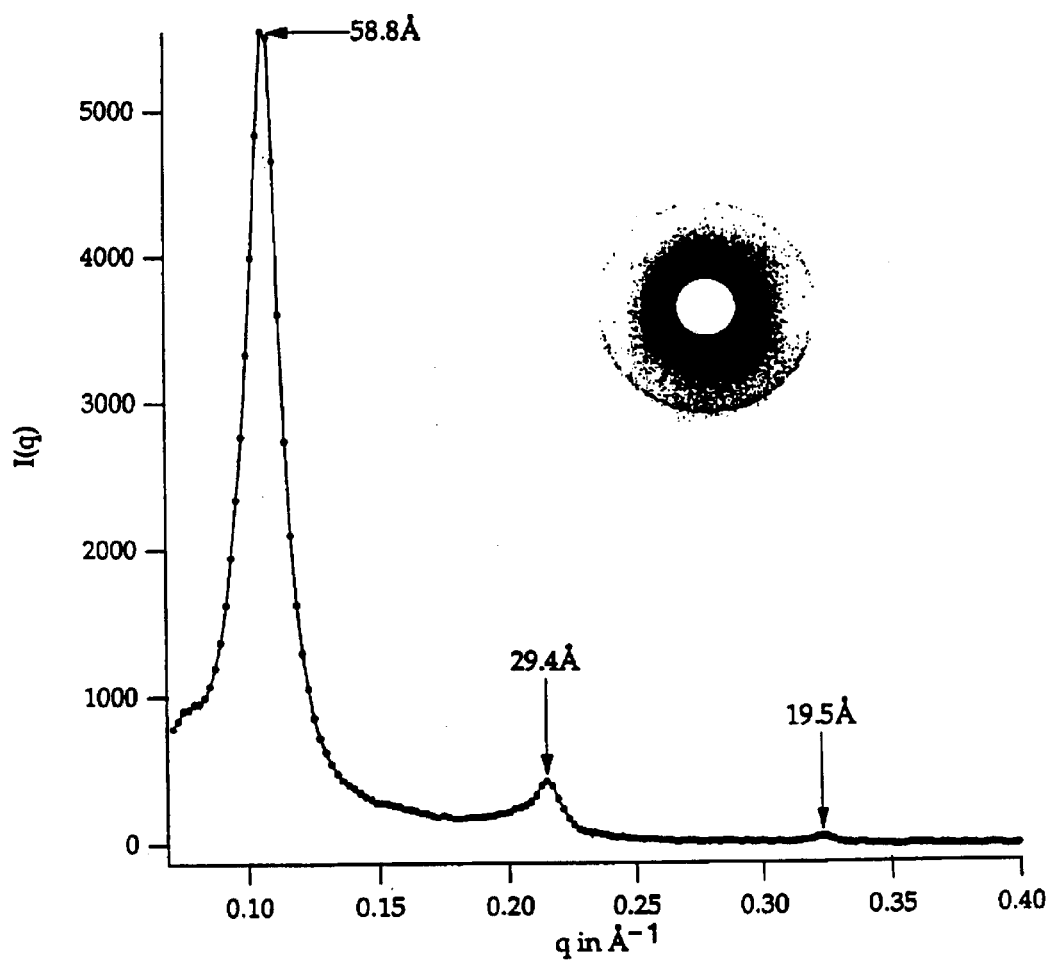
FIG. 8. Plot of the radially averaged intensity of DOTAP:Chol-DNA liposome complexes versus scattering wave-vector q. The DOTAP:Chol DNA liposome complexes show the x-ray diffraction maximum, 58.8A, that confirms the thickness of DNA+lipid determined by cryo-electron microscopy.

For example, DNA binding reduces the surface area of the outer leaflet of the bilayer and induces the negative curvature due to lipid ordering and reduction of charge repulsion between cationic lipid headgroups. Condensation of the internalized lipid sandwich expands the space between the bilayers and may induce membrane fusion to generate the apparently closed structures in FIGS. 3B, D. Interaction of more than two liposomes may create the more complex structures seen in this micrograph. The predicted thickness of 10.5 nm for DNA sandwiched between 2 bilayers (FIGS. 3D, G) is in agreement with observed measurements of these areas as shown in FIG. 3B. In addition, the thickness of DNA+lipid is confirmed by small angle x-ray scattering analyses (FIG. 8).

Alloying soft bilayers that contain dioleoyl chains with cholesterol is known to increase the stretching elastic modulus by up to an order of magnitude (Lasic and Needham (1995)). Liposomes that have mechanically weaker bilayers cannot efficiently undergo an inversion, and the agent complexed to these liposomes is less protected in the circulation. The presence of appropriate levels of cholesterol in the bilayer provides sufficient strength to liposomes for efficient "vase" formation. The size, mechanical strength, and flexibility of the lipid vesicles as well as the biologically active agent-liposome ratio are critical for this self-assembly mechanism of DNA condensation on the interior of invaginated liposomes. This model predicts that an approximate $\rho$ value of 2 will be preferred to neutralize all charge associated with the biologically active agent by generating the lipid bilayer "sandwich". This also demonstrates that the outside of the sandwich liposome complexes will be positively charged and free of biologically active agent.

The present invention clearly shows that cholesterol is an efficient neutral lipid in a liposome complex for in vivo DNA delivery. High content of cholesterol is known to increase the stability of liposomes. The presence of cholesterol stabilizes bilayers and complexes in the plasma against mechanical breakage upon adsorption of plasma components. In addition, DOTAP is an effective cationic lipid. The combination of DOTAP:Chol to produce cationic liposomes under the specific method of the present invention resulted in liposomes with unique and useful properties for in vivo gene delivery. The present invention provides an up to 150-fold improvement in gene expression in several organs using extruded DOTAP:Chol liposomes for systemic DNA delivery as compared with prior art techniques. This vast improvement allows increased efficiency of gene transfer in vivo.

Unlike other cationic liposomes, DOTAP:Chol liposomes, in one embodiment, form stable DNA complexes over a broad range of DNA:liposome ratios. This flexibility allows optimization of the complexes for in vivo delivery to different tissues. Most tissues other than lung are very sensitive to this ratio (corresponding to $\rho=2$); therefore, this ratio must be carefully optimized for each DNA concentration. The stability of DOTAP:Chol at high concentrations of liposome and DNA allows for increased concentrations of DNA to be delivered and expressed. An effective liposome system must protect DNA in the circulation, yet be able to deliver the DNA effectively to tissues. These properties have been achieved with the DOTAP:Chol liposomes as a result of their more cohesive bilayer and their ability to internalize and therefore protect DNA.

The following examples serve to illustrate further the present invention and are not to be construed as limiting its scope in any way.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention and others can, by applying current knowledge, readily modify and/or adopt for various applications such specific embodiments without departing from the generic concept, and therefore such adaptations and modifications are intended to be comprehended within the meaning and range of equivalents of the disclosed embodiments.

All of the references mentioned in the present application are incorporated in toto into this application by reference thereto.

EXAMPLE 1

DOTAP:Chol liposomes, as well as other liposome formulations, were prepared using the following procedure: the cationic lipid (DOTAP or DDAB) was mixed with the neutral lipid (Chol or DOPE) at equimolar concentrations. The mixed powdered lipids were dissolved in HPLC-grade chloroform (Mallinckrodt) in a 1 L round bottomed flask. The clear solution was placed on a Buchi rotary evaporator at 30° C. for 30 min to make a thin film. The flask containing the thin lipid film was dried under vacuum for 15 min. The film was hydrated in 5% dextrose in water ("D5W") to give a final concentration of 20 mM DOTAP (or 20 mM DDAB) and 20 mM Chol (or 20 mM DOPE), and is referred to as 20 mM DOTAP:Chol. The hydrated lipid film was rotated in a 50° C. H$_2$O bath for 45 min and then at 35° C. for an additional 10 min. The mixture was allowed to stand in the parafilm-covered flask at room temperature overnight. On the following day, the mixture in the flask was sonicated for 5 min at 50° C., transferred to a tube, and was heated for 10 min at 50° C. The mixture was sequentially extruded through decreasing size filters: 1 $\mu$m, 0.45 $\mu$m, 0.2 $\mu$m, and 0.1 $\mu$m (Whatman) using syringes. Whatman Anotop filters, 0.2 $\mu$m and 0.1 $\mu$m, were used. Portions of the liposome mixture that did not pass through the first 0.1 $\mu$m filter, were heated again at 50° C. for 5 min before passing through a new 0.1 $\mu$m filter. Filtered fractions were pooled and stored under argon gas at 4° C. DOTAP and DOPE were purchased from Avanti Polar Lipids. DDAB was purchased from Sigma Chemical Company, and highly purified cholesterol was purchased from Calbiochem.

EXAMPLE 2

DNA-Sandwich Liposomes

DNA:liposome complexes were prepared the day prior to their use in an animal host. DNA was diluted in D5W (5% dextrose in water), and stock liposomes were diluted in D5W to produce various ratios of DNA:liposomes. The final volumes of both the DNA solution and the liposome solution used for mixing were equal. Dilutions and mixings were performed in 1.5 ml Eppendorf tubes with all reagents at room temperature. The DNA solution was added rapidly at the surface of the liposome solution using a pipette tip. The DNA:liposome mixture was mixed rapidly up and down twice using a Pipetman. DNA:liposome complexes were stored overnight at 4° C.

The protocol used for DNA preparation, referred to herein as the Debs protocol, is a variation of the alkaline lysis procedure described by Maniatis (Sambrook et al. (1989)), and includes a 2 hour Proteinase K digestion step immediately following RNase A digestion. This method consistently produced about 20-fold greater amounts of DNA than the alkaline lysis procedure followed by polyethylene glycol (PEG) precipitation, and yields were in the range of 10 to 28 mg of plasmid DNA per liter of bacterial culture. This DNA preparation protocol resulted in no toxicity of DNA:liposome complexes in mice. Endotoxin levels of DNA prepared by the different methods were determined using the chromogenic limulus amebocyte lysate assay (Kinetic-QCL; BioWhittaker). Endotoxin levels of 120 Endotoxin Units (EU)/μg DNA, 16 EU/μg DNA, and 8 EU/μg DNA were determined for the Maniatis alkaline lysis method followed by PEG precipitation, the Qiagen Maxi-prep Kit, and the Debs protocol for preparation of plasmid DNAs, respectively. No genomic DNA, small DNA fragments, or RNA were detected in the DNA prepared by the Debs protocol, and the $OD_{260/280}$ ratios of all plasmid DNA preparation were 2.0.

EXAMPLE 3

In Vivo Administration of DNA-Sandwich Liposomes

For in vivo intravenous administration, 6-weeks old (~20 g) BALB/c mice were injected in the tail vein with 200 μl of DNA:liposome complexes using a 27-gauge syringe needle. Samples were placed at room temperature for 1 hour prior to tail vein injection. Mice were sacrificed 24 hours post-injection, and the organs were harvested and quickly frozen on liquid nitrogen. Tissue extracts were prepared as previously described (Stribling et al. (1992)). Lymph node extracts consisted of pooled mesenteric, axillary, iliac, submandibular, and inguinal lymph nodes. ELISAs were performed using the Boehringer Mannheim CAT ELISA kit. All CAT protein determinations were corrected for any CAT immunoreactivity detected in control tissues, and the lowest levels of CAT protein reported for any experimental tissues were at least 3-fold higher than background. Protein determinations were performed using the Micro BCA kit (Pierce). This work was conducted in accordance with NCI/FCRDC guidelines using an approved animal protocol.

In order to demonstrate that the DNA is protected within the liposome, DNA-sandwich liposomes can be subjected to filtration through polysulfone filters of various pore sizes. The liposomes maintain full activity through the 1.0 μm and 0.45 μm filters, demonstrating that the DNA is fully sequestered and protected from the exterior. (See Table 1) If the DNA had been attached to the outside of the liposome, its protein expression activity would have been lost by filtering, since polysulfone strips DNA from complexes carrying it on the outside.

Table 1 also illustrates that the DNA-sandwich liposomes capable of efficient DNA delivery are preferably larger than 200 nm in size. Particularly preferred DNA-sandwich liposomes include those between 200 nm and 450 nm in size. The exact size may vary with the DNA contained therein, the route of administration and the condition being treated. The skilled artisan can readily determine the appropriate size complexes based upon these parameters.

TABLE 1

CAT production in organs using size fractionated DNA: liposome complexes

| | Total CAT protein produced (ng)* | | | |
|---|---|---|---|---|
| Organ | No Filtration | 1.0 μm Filtration | 0.45 μm Filtration | 0.2 μm Filtration |
| Lung | 168.6 | 207.0 | 154.8 | 68.4 |
| Heart | 8.5 | 7.6 | 6.6 | 1.8 |
| Liver | 5.5 | 4.6 | 6.0 | 2.4 |
| Muscle (quadricep) | 5.0 | 6.0 | 5.7 | 1.5 |
| Kidney | 1.0 | 1.6 | 1.2 | 0.6 |
| Thymus | 0.9 | 0.8 | 1.2 | 0.1 |
| Colon | 0.4 | 0.7 | 0.9 | 0.6 |
| Spleen | 0.2 | 0.2 | 0.3 | 0.1 |
| Lymph nodes | 0.1 | 0.1 | 0.1 | 0.03 |
| Brain | 0.1 | 0.1 | 0.2 | 0.1 |

*Total CAT protein was determined by ELISA for organs harvested 24 hours post-injection. Mice were injected with 3 mM DOTAP:Chol + 100 ug of CAT plasmid DNA filtered through the indicated pore size after liposome:DNA mixing. Results are the mean of duplicate analyses determined using two animals in each group.

EXAMPLE 4

Comparison of Liposome Combinations

In order to demonstrate the unexpected nature of the present invention, the capacity of different liposome formulations to form complexes with DNA was examined. Various concentrations of liposomes were mixed with DNA in a final volume of 200 μl, and the absorbance at 400 nm was determined for 1:20 dilutions of each sample. The DNA:liposome phase diagram showed that DOTAP containing liposomes stably complexed large amounts of DNA over a wide range of DNA:liposome ratios (FIG. 1A). Soluble complexes using DDAB liposomes had lower maximal DNA concentrations and were stable over a narrow range using either DOPE or Chol. A maximum of 82.5 μg of DNA was optimally complexed with 5 mM DDAB formulations in a 200 μl final volume without causing precipitation.

Figure 1B:
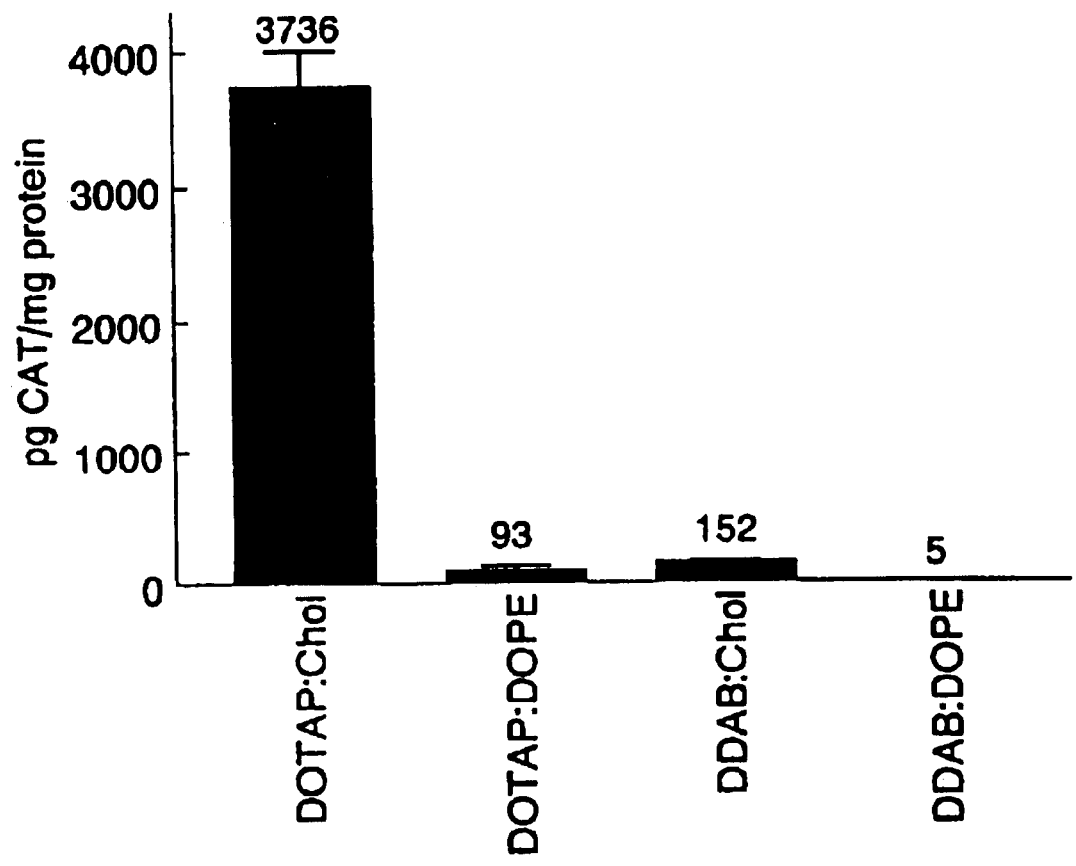
FIG. 1B. Production of Chloramphenicol Acetyl Transferase ("CAT") in the mouse lung following systemic delivery using a variety of DNA:liposome formulations. Each mouse was injected with 82.5 μg plasmid DNA:5 mM liposome (5 mM cationic lipid+5 mM neutral lipid), the optimal DNA:lipid ratio for the DDAB (Dimethyldioctadecylammonium Bromide) formulations. CAT expression was normalized to protein concentration in the tissue extracts and is presented as the mean+/−Standard Error of the Mean ("SEM") of duplicate determinations.

On the basis of their physicochemical properties, these liposome formulations were complexed to DNA and introduced into mice by tail vein injection. Systemic DNA delivery and gene expression were compared using 1:1 formulations of DDAB:Chol, DDAB:DOPE, DOTAP:Chol, and DOTAP:DOPE liposomes, each at 5 mM, complexed to 82.5 μg plasmid DNA in a 200 μl final volume. This DNA:liposome ratio was found to be optimal for in vivo expression of DNA delivered by DDAB:Chol liposomes (Liu et al. (1995)). At 24 hours postinjection the mice were sacrificed, and the levels of CAT production in the lung were determined (FIG. 1B). Both extruded and non-extruded preparations of the above lipid formulations were injected into mice and the results compared to each other and to those obtained by other investigators. The non-extruded liposome preparations resulted in lower expression in all cases compared to the corresponding extruded preparations. CAT production using DDAB:Chol liposomes prepared by sonication without extrusion, was in excellent agreement with CAT production reported using the same conditions (Liu et al. (1995)), based on the specific activity of CAT at 100,000 U per mg per min.) and the identical plasmid (The CAT plasmid used in all experiments were p4119 (Liu et al. (1995)). Using additional heating and extrusion steps (see Example 1) in the preparation of DDAB:Chol liposomes prior to mixing with DNA, increased expression 2-fold.

Interestingly, the extruded DOTAP:Chol-DNA liposome complexes produced 50-fold greater amounts of protein expression in the lung compared to the highest levels that have been reported using sonicated DDAB:Chol in the same tissue (Liu et al. (1995)). In addition, the level of CAT protein produced in the lung using this novel formulation was greater than 50-fold compared to that using sonicated DOTMA:DOPE (DOTMA is N-[1-(2,3-dioleyloxy)propyl]-N,N,N-trimethylammonium chloride (also known as Lipofectin™)) (Zhu et al. (1993)) or sonicated DOTIM:Chol (DOTIM is 1-[2-(9(Z)-Octadecenoyloxy)ethyl]-2-(8(Z)-heptadecnyl)-3-(2-hydroxyethyl)imidazolinium chloride) (Solodin et al. (1995)). Extruded DOTAP:DOPE-DNA liposome complexes and extruded DDAB:DOPE-DNA liposome complexes produced far less CAT in the lungs compared to DOTAP:Chol-DNA liposome complexes.

Figure 2A:
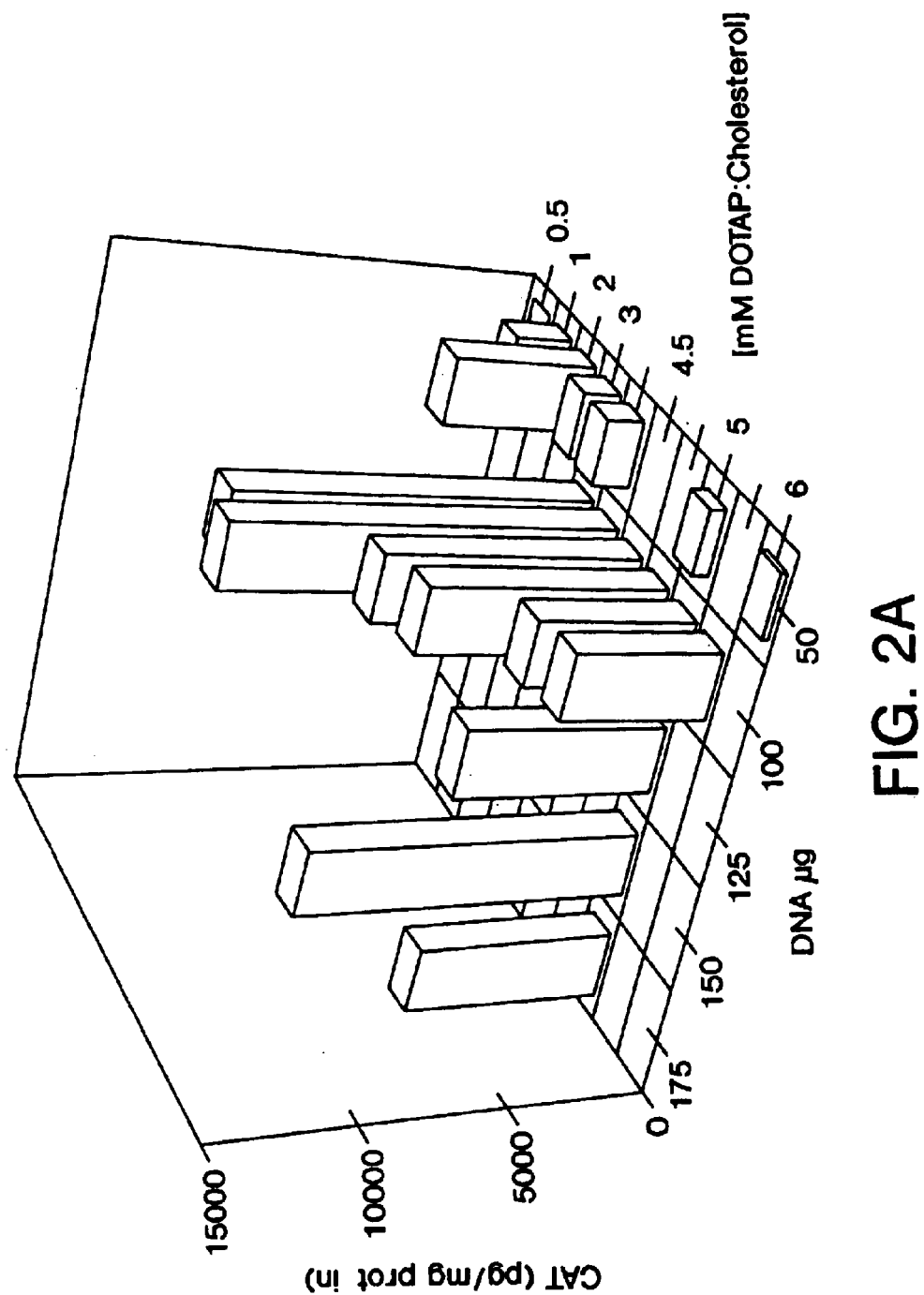
FIG. 2A. CAT production in vivo following systemic delivery of DOTAP:Chol-DNA complexes. Dose response in the lung using various DOTAP:Chol-DNA:liposome ratios. The concentrations of DOTAP:Chol varied from 0.5 mM to 6 mM complexed with 50 to 175 μg DNA per tail vein injection. (All mM liposome concentrations refer to the cationic lipid or the neutral lipid; therefore, 6 mM DOTAP:Chol=6 mM DOTAP+6 mM Chol.) 5 mM DOTAP:Chol was complexed to 50, 100, 125, 150, and 175 μg DNA. At 100 μg DNA, DOTAP:Chol was complexed at 5.5 mM, 5 mM, 4.75 mM, 4.5 mM, 4 mM, and 3 mM. At 50 μg DNA, DOTAP:Chol was complexed at 6 mM, 5 mM, 4 mM, 3 mM, 2 mM, 1 mM, and 0.5 mM. The data points shown here are averages of CAT production from 40 mouse lungs. Each data point is at least a duplicate determination, and some data points were averages of 4 assays with standard errors varying from 1% to 18% of the mean. White boxes indicate data points not determined.

To determine whether other extruded DOTAP:DOPE formulations would improve delivery by using the optimal DNA:liposome ratio for the lungs, 4 mM DOTAP:DOPE complexed to 100 µg of DNA were injected into mice. CAT production remained 50-fold lower than that observed with 4 mM DOTAP:Chol-DNA liposome complexes (FIG. 2E). In addition, CAT production was determined using other extruded liposome formulations including 4 mM DOTAP-DNA liposome complexes, 4 mM DOTAP:Chol: Dioleoyl Phosphatidylserine (DOPS)-DNA liposome complexes, and 4 mM DOTAP:Oleoyl Phosphatidylcholine (DOPC)-DNA liposome complexes. As shown in FIG. 2E, DOTAP and all other formulations were not as effective as DOTAP:Chol for gene expression in vivo, and these formulations did not provide as broad a biodistribution as that using DOTAP:Chol (data not shown). Addition of small amounts of DOPS, 5%, to DOTAP:Chol (50:45) dramatically reduced in vivo gene expression (FIG. 2E), and use of DOPC instead of Chol eliminated in vivo gene expression almost entirely (FIG. 2E). Both DOPS and DOPC contain large headgroups and could perhaps interfere with the DNA:liposome assembly shown in our model (FIG. 4).

EXAMPLE 5

In order to evaluate in vivo expression, 100 µg of DNA were mixed with varying concentrations of DOTAP:Chol. The highest levels of CAT were produced in lungs using 3 mM and 4 mM DOTAP:Chol complexed to 100 µg DNA, with an approximate +/− charge ratio $\rho=2$. However, significant expression was obtained at all ratios (FIG. 2A). Furthermore, the maximal expression using 100 µg DNA was greater in lungs than that produced from injections of 5 mM DOTAP:Chol complexed to 150 µg DNA, and this expression was approximately 100-fold greater than previously reported using other cationic liposomes (Zhu et al. (1993); Philip et al. (1993); Solodin et al. (1995); Liu et al. (1995) based on the specific activity of CAT at 100,000 U per mg per min.). In addition, complexes of 3 mM to 4 mM DOTAP:Chol mixed with 100 µg DNA were stable upon storage at 4° C. for longer periods than complexes mixed with 125 µg and 150 µg DNA at optimal DNA:liposome ratios. To determine whether DOTAP:DOPE formulations would improve delivery by using the optimal DNA:liposome ratio, 3 mM DOTAP:DOPE complexed to 100 µg DNA were injected. However, the levels of CAT produced remained 50-fold lower than that produced by 3 mM DOTAP:Chol-DNA liposome complexes.

EXAMPLE 6

Using different concentrations of DOTAP:Chol complexed to 50 µg of DNA, there were more dramatic differences in the dose-response in the lung as compared to formulations containing higher amounts of DNA. Optimal production of CAT in the lung was observed after injection of complexes containing 2 mM DOTAP:Chol complexed to 50 µg of DNA (FIG. 2A). Thus, optimal expression at all DNA concentrations was achieved at comparable DNA:liposome ratios namely approximate +/− charge ratio $\rho=2$. However, the lower colloidal concentration of DNA and liposomes using 50 µg DNA reduced the expression levels even at the optimal DNA:liposome ratio. In addition, CAT production fell sharply at DNA:liposome ratios either lower or higher than the optimum.

To assess the amount of protein expressed in each tissue, total protein production was calculated for animals receiving 3 mM or 4 mM DOTAP:Chol complexed to 100 µg DNA (Table 2). Data showed that high levels of gene expression could be obtained using DOTAP:Chol as a systemic delivery vehicle. Although expression in lung was relatively insensitive to the ratio of DNA:liposome, most other tissues showed a 2 to 4-fold decrease in protein production using 4 mM instead of 3 mM DOTAP:Chol. Thus, the greater sensitivity to DNA:liposome ratio noted for heart in FIG. 2C may apply to most tissues other than the lung.

TABLE 2

Effect of DNA: lipid ratio on organ distribution of protein production.

| Organ | Total CAT Protein produced (ng)* | |
|---|---|---|
| | 3 mM DOTAP:Chol | 4 mM DOTAP:Chol |
| Lung | 170.4 | 166.8 |
| Heart | 8.7 | 3.5 |
| Liver | 5.6 | 3.4 |
| Muscle (quadricep) | 5.1 | 1.8 |
| Kidney | 0.9 | 0.6 |
| Colon | 0.4 | 0.1 |
| Spleen | 0.3 | 0.1 |
| Lymph Nodes | 0.2 | 0.1 |
| Thymus | 0.2 | 0.1 |
| Brain | 0.2 | 0.1 |

*Total CAT protein was determined by ELISA for organs harvested 24 hours post-injection. Mice were injected with 100 µg CAT plasmid complexed with the indicated concentrations of DOTAP: cholesterol. Results are the mean of duplicate analysis determined using two animals in each group.

EXAMPLE 7

Because the in vitro data showed that DOTAP:Chol formed stable colloidal complexes over a wide range of DNA:liposome ratios (FIG. 1A), different groups of mice were injected with complexes consisting of 0.5 mM to 6 mM DOTAP:Chol mixed with 50 to 175 µg DNA in a 200 µl final volume. The goal was to determine the optimal DNA:liposome ratio for the DOTAP:Chol system. Results from initial experiments showed that DNA delivery and gene expression were further increased by optimizing this DNA:liposome ratio. Maximal CAT production in mouse lung was produced by the use of 3–4 mM DOTAP:Chol complexed to 100 µg DNA (corresponding to a +/− charge ratio $\{\rho\}$ of 2, FIG. 2A). The highest level of CAT production was approximately 100-fold greater than previously achieved (Zhu et al. (1993); Philip et al. (1993); Solodin et al. (1995); Liu et al. (1995)). The CAT activity was based on the specific activity of CAT at 100,000 U per mg per min. Although higher amounts of DNA formed stable complexes with these liposomes, toxicity was induced after 200 µl injections of 250 and 300 µg DNA complexed with 9 mM and 10 mM DOTAP:Chol, respectively.

EXAMPLE 8

Tissue Expression Levels

Figure 2B:
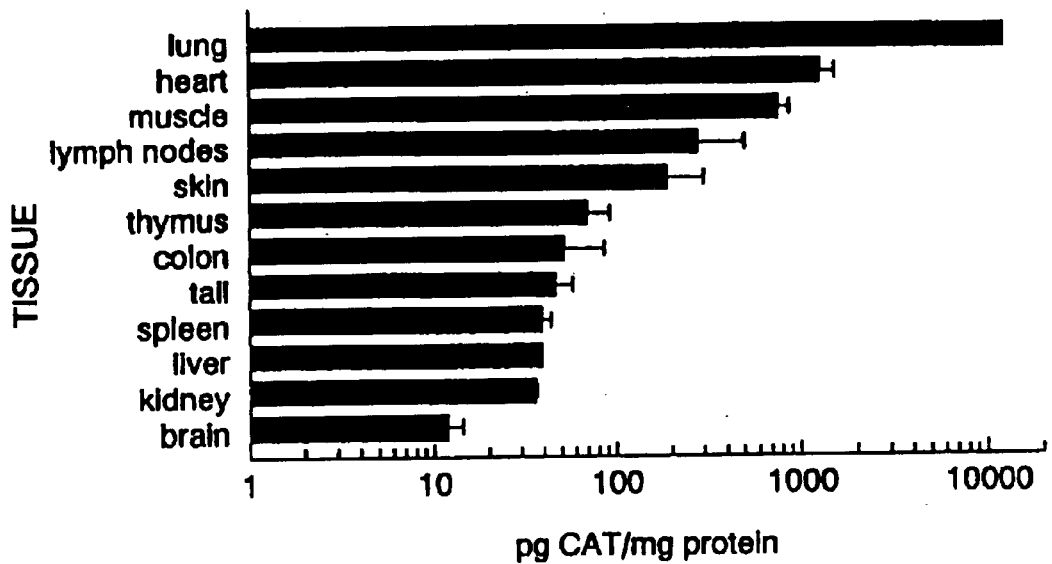
FIG. 2B. CAT production in various tissues using 3 mM DOTAP:Chol complexed with 100 μg DNA per tail vein injection. CAT expression was normalized to protein concentration in the tissue extracts and is presented as the mean+/−SEM.
Figure 2C:
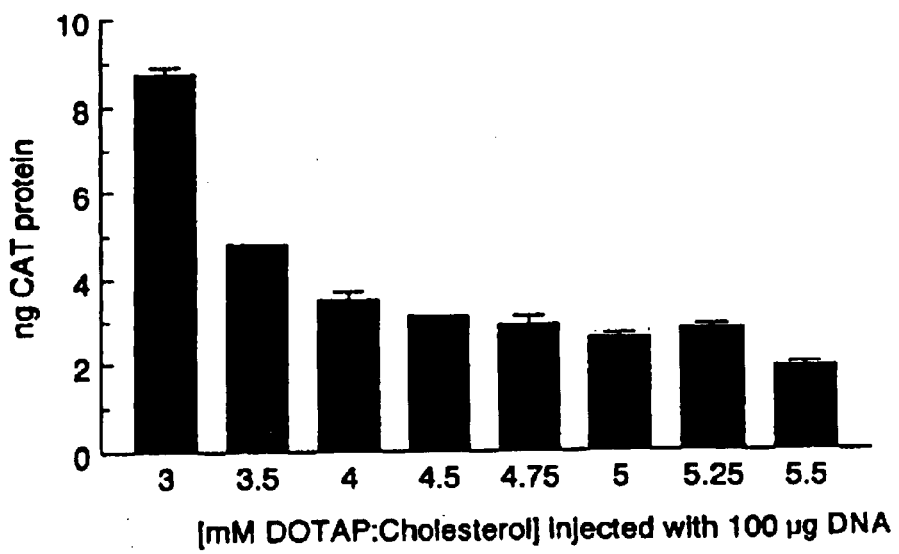
FIG. 2C. Dose response in the heart using various DNA:liposome ratios showing total CAT production. The concentrations of DOTAP:Chol varied from 3 mM to 5.5 mM complexed with 100 μg DNA per tail vein injection.

Using the optimal DNA:liposome ratio and colloidal concentration for the DOTAP:Chol system identified in these experiments, (3 mM DOTAP:Chol complexed to 100 µg DNA), CAT production in other tissues was studied (FIG. 2B). Significant amounts of CAT were produced in all tissues examined (FIG. 2B). Approximately 75 to 150-fold greater amounts of CAT were produced in the lung, heart, liver, muscle, and kidney than previously reported using other cationic lipids (Zhu et al. (1993); Philip et al. (1993); Solodin et al. (1995); Liu et al. (1995)) based on the specific activity of CAT at 100,000 U per mg per min. Expression in the heart was optimal at 3 mM DOTAP:Chol+100 µg DNA and decreased markedly at other ratios (FIG. 2C). For lymph nodes and spleen, the levels of CAT protein produced were about 25-fold and 2-fold greater than prior reports, respectively. CAT production in all tissues was determined for every formulation. It was found that CAT production was optimal using 3 mM DOTAP:Chol complexed to 100 µg DNA in all tissues except for lymph nodes. Gene expression in lymph nodes was optimal using 5 mM DOTAP:Chol complexed to 150 µg DNA, and CAT production was increased 75-fold over that previously reported. Quantitation of CAT production has not been previously reported in the thymus, skin, tail, colon, and brain, although expression has been noted in some of these tissues (Zhu et al. (1993); Philip et al. (1993); Solodin et al. (1995); Liu et al. (1995); Thierry et al. (1995)).

Figure 2D:
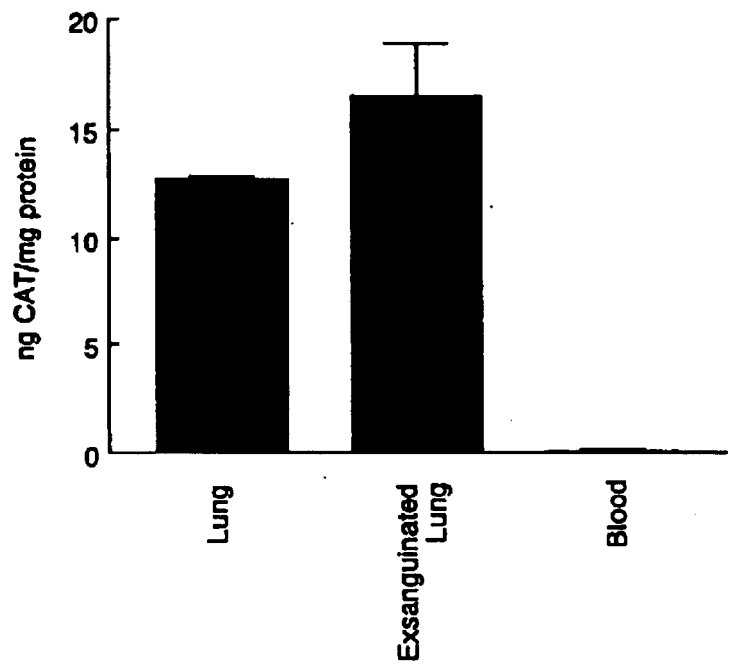
FIG. 2D. Comparison of CAT production levels in the lungs of mice exsanguinated prior to organ harvest and mice that were not bled. In addition, whole blood was assayed. CAT activity in the lung is due to gene expression in tissue rather than in blood. CAT expression was normalized to protein concentration in the tissue extracts and is presented as the mean+/−SEM.
Figure 2E:
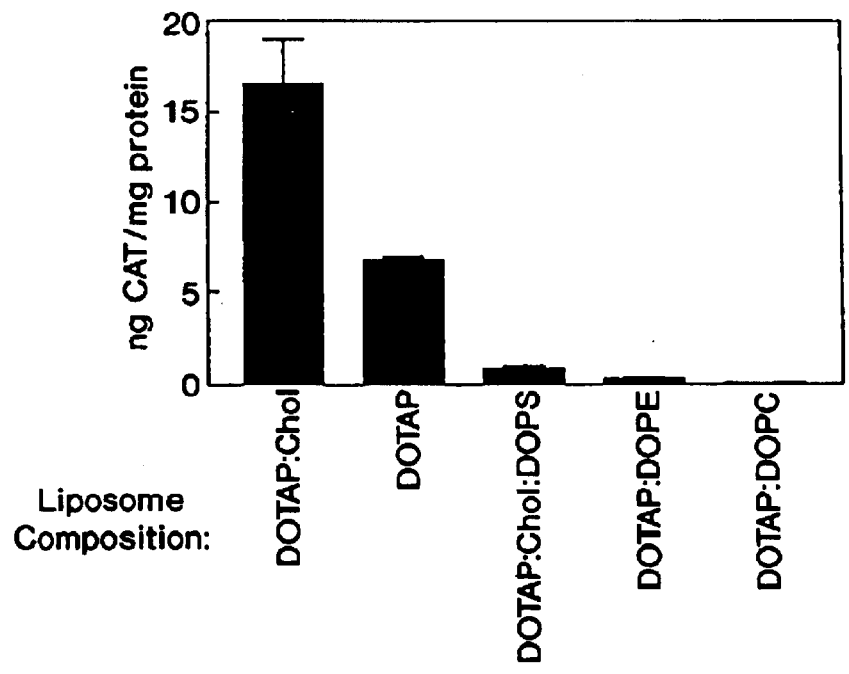
FIG. 2E. Comparison of CAT production in the lungs of exsanguinated mice using different DOTAP formulations. All of the following formulations shown used 4 mM DOTAP: DOTAP:Chol (50:50), DOTAP, DOTAP:Chol:D-OPS (50:45:5), DOTAP:DOPE (50:50), and DOTAP:DOPC (50:50). "DOPS" is dioleoyl (18:1) phosphatidyl serine "DOPC" is oleoyl (18:1) phosphatidyl choline (9-cis) octadecanoic acid. All formulations were complexed to 100 μg of DNA in a 200 μl final volume. CAT expression was normalized to protein concentration in the tissue extracts and is presented as the mean+/−SEM.

If nucleated cells in the blood were transfected by the systemically delivered complexes, expression of CAT in some tissues may result from blood included in the specimens. This was not the case in the lung, because CAT production in whole blood, 47 pg/mg total protein, was much lower than in the lungs obtained from the same mice (FIG. 2D). Furthermore, CAT concentration measured in the lungs of exsanguinated mice was elevated about 30%, because the total protein levels were lower in the absence of blood. CAT levels for most other tissues from the exsanguinated mice showed either increased concentrations of CAT or concentrations similar to nonbled mouse tissues. CAT concentration levels decreased in the tail, skin, and brain for samples assayed from exsanguinated mice, suggesting that CAT production detected in these tissues may, in part, be contributed by nucleated blood cells.

EXAMPLE 9

Targeting Ligands

Succinylated asialofetuin was made as previously described (Kaneo et al. (1991)), and 4 mM DOTAP:Chol was complexed with 100 µg of DNA in a 200 µl final volume. These complexes were filtered through a 0.45 µm polysulfone filter (Whatman). Succinylated asialofetuin, to yield a final concentration of 0.2 mg/ml, was added to these filtered DNA:liposome complexes using a Pipetman pipet tip. This mixture was mixed slowly up and down twice in the pipet tip. DNA:liposome complexes were stored overnight at 4° C. No precipitation of the DNA:liposome-asialofetuin complexes occurred. These complexes were injected into the tail vein of mice as described above.

Succinylated asialofetuin is highly negatively-charged; therefore, it can bind tightly to the positively charged surface of liposomes that contain DNA between the invaginated liposomes. There was a dose-dependent rise in the $OD_{400}$ after addition of succinylated asialofetuin. The absorbance at 400 nm was determined for 1:20 dilutions of the following DNA:liposome complexes with or without succinylated asialofetuin. DOTAP:Chol-DNA liposome complexes had an $OD_{400}$ of 0.815; and DOTAP:Chol-DNA+0.1 g/ml succinylated asialofetuin and DOTAP:Chol-DNA+0.2 mg/ml succinylated asialofetuin had $OD_{400}$ readings of 0.844 and 0.873, respectively. Addition of succinylated asialofetuin at amounts greater than 0.2 mg/ml produced immediate precipitation of DNA:liposome complexes. These observations show that succinylated asialofetuin strongly interacts with the DOTAP:Chol-DNA liposome complexes. Succinylated asialofetuin was added to the surface of the liposome complexes to achieve greater gene expression in the liver. Asialofetuin is an asialoglycoprotein containing terminal galactosyl residues and has been used to efficiently target liposomes to the liver. (Spanjer and Scherphof (1983); Spanjer et al. (1984); Dragsten et al. (1987); Murahashi and Sasaki (1996); Hara et al. (1995)). In addition, changing the surface charge on the outside of the DNA:liposome complexes to reduce ionic interactions with endothelial proteoglycans (Mislick and Baldeschwieler (1996)) may also facilitate organ-specific delivery.

Figure 7:
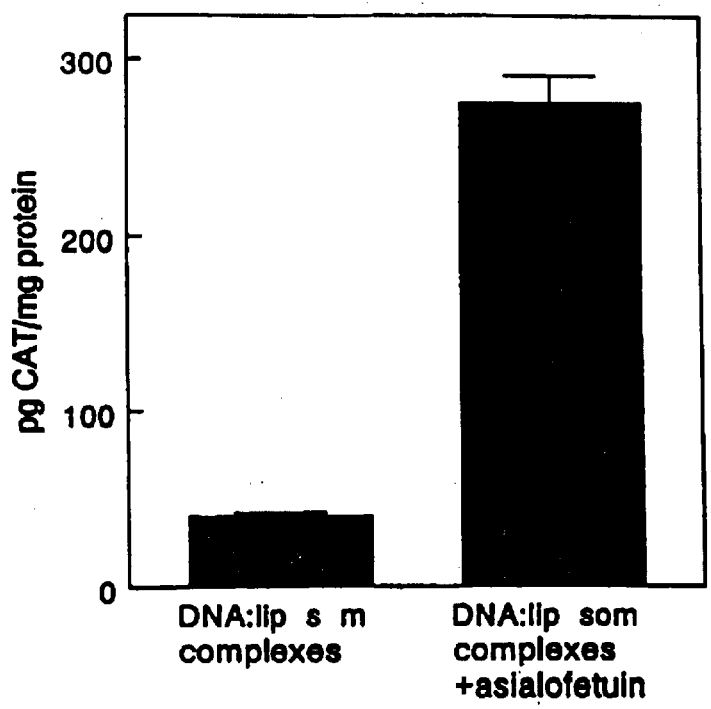
FIG. 7. CAT production in the mouse liver at 24 hours after tail vein injection using DNA:liposome complexes coated with succinylated asialofetuin. Each mouse was injected into the tail vein with 4 mM DOTAP:Chol complexed to 100 μg of DNA in a 200 μl final volume with or without addition of succinylated asialofetuin after DNA:liposome mixing. CAT expression was normalized to protein concentration in the tissue extracts and is presented as the mean+/−SEM of duplicate determinations.
Figure 6:
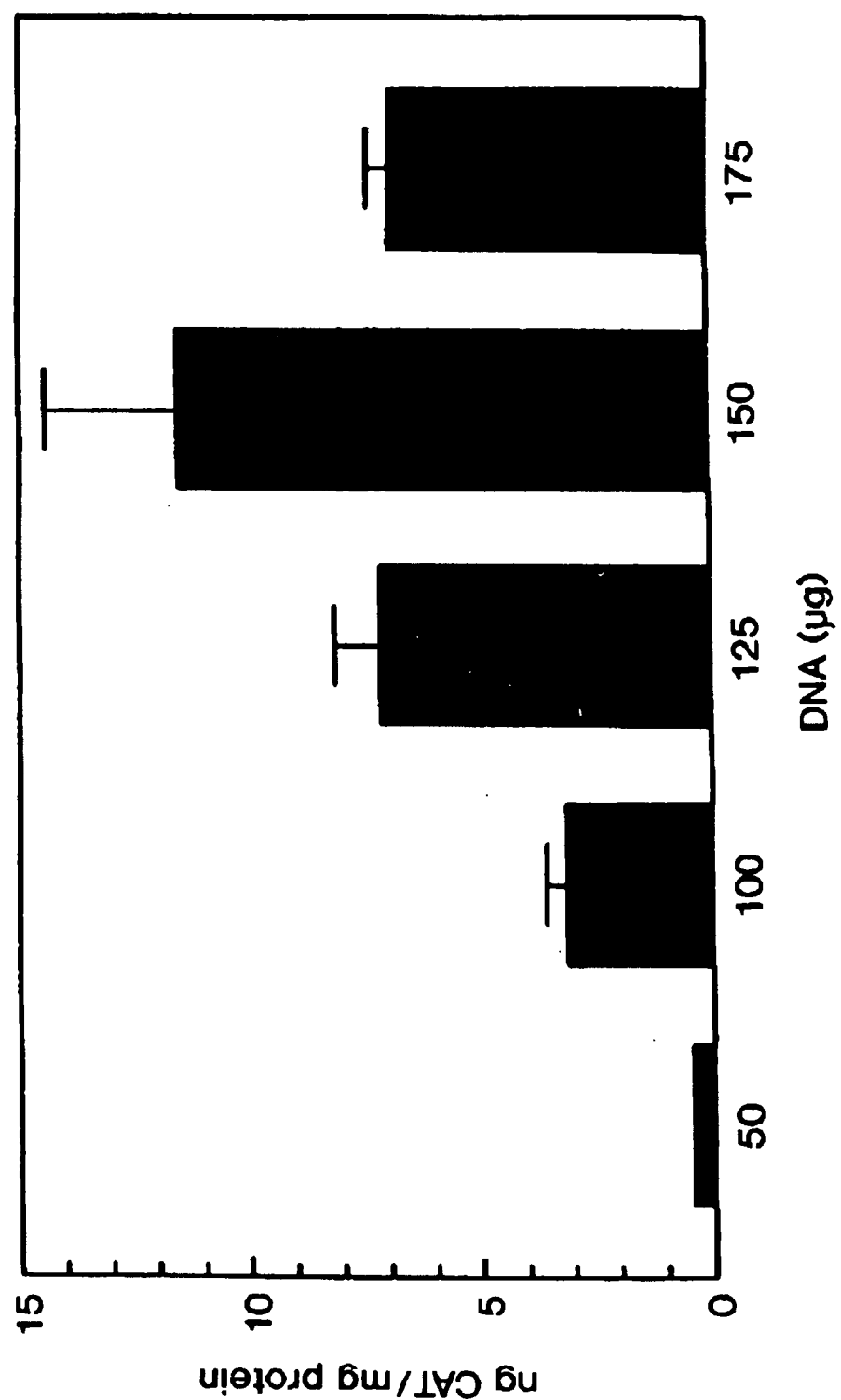
FIG. 6. Production of CAT in the mouse lung following systemic delivery using 5.0 mM DOTAP:Chol complexed to a variety of DNA amounts per tail vein injection. 5.0 mM DOTAP:Chol may be complexed to a wide range of plasmid DNA concentration without precipitation of the DNA:liposome complexes. Mice were injected with liposomes that contained 50 μg, 100 μg, 125 μg, 150 μg and 175 μg of DNA plasmid per tail vein injection. It is not common for any liposome formulation to be highly tolerant over a wide range of DNA:liposome ratios; therefore, our DOTAP:Chol liposomes are extremely unique in this regard. Furthermore, the present invention demonstrates a dose response in vivo using different amounts of DNA injected. At 150 μg DNA, the highest production of CAT was produced in the lung, and that level of CAT production is up to 150-fold greater than any reported in the literature.

Addition of succinylated asialofetuin to preformed DNA:liposome complexes provided a ligand for the hepatic asialoglycoprotein receptor (Ashwell and Harford (1982)) and increased CAT production in the liver seven-fold (FIG. 7). This targeting was specific for the liver, as CAT expression in other organs shown in FIG. 2B was not increased. This widely used ligand was employed solely to demonstrate feasibility of the present method for adding ligands.

EXAMPLE 10

Cyro-Electron Microscopy

Thin films were prepared by dipping and withdrawing a 700-mesh copper grid (3 mm diameter, 3 to 4 µm thick) in the liposome or the DNA:liposome suspensions. After excess liquid was removed by blotting, the thin films that formed between the bars of the grid were vitrified in melting ethane. After cryotransfer, the specimen was observed at −170° C. in a Philips CM 12 microscope at low dose, 120 kV 19.

To examine the mechanism of the high in vivo gene delivery, the DNA-sandwich:liposome complexes were examined by studying their morphology as well as that of non-DNA associated liposomes with cryo-electron microscopy. Extruded DOTAP:Chol liposomes in the absence of DNA showed many completely invaginated liposomes with two concentric lamellae and a small orifice. Most liposomes were spherical with an approximate diameter of 50 nm.

Vase structures represented one-third of the entire liposome population. Large tubular structures were also observed, explaining the somewhat larger size of approximately 240 nm, determined by dynamic light scattering using a Coulter N4 particle size analyzer.

Figure 3E:
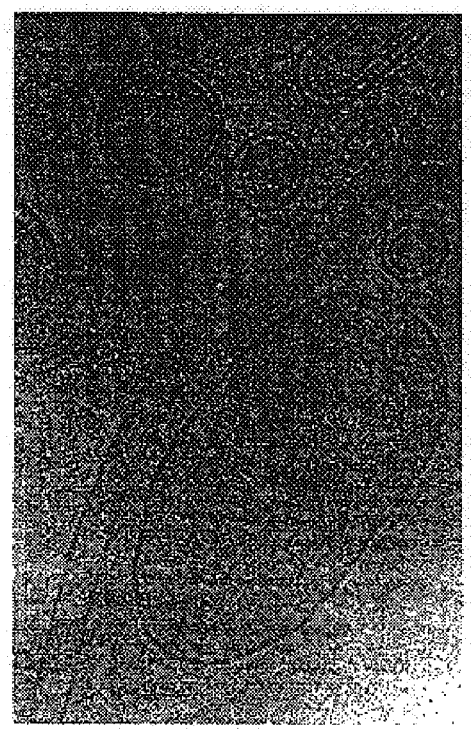
Figure 3F:
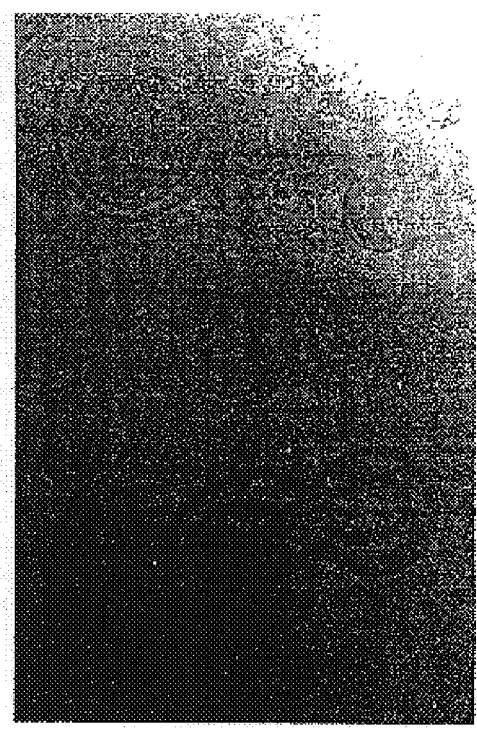

When these liposomes were complexed with DNA at optimal concentrations, with a +/− charge ratio ρ=2 (Lasic et al. (1997)), the DNA was localized to the interior of the liposomes (FIG. 3B). DOTAP:DOPE (dioleoyl phosphatidyl-ethanolamine) and DOTAP:Chol complexes with DNA were turbid colloidal solutions with mean particle size of 445 nm and 405 nm, respectively. Particle size did not depend on dilution, and turbidity obeyed Beer Lambert Law indicating stability of these complexes in vitro. DOTAP:DOPE liposomes also form "vase structures"; however, the orifices were larger and many spheres were formed (FIG. 3E). In addition, there were many structures with little or no DNA assembled in the extruded DOTAP:DOPE liposomes (FIG. 3F), and the DNA was frequently found on the outside of these liposomes (FIG. 3F). DDAB:DOPE and DDAB:Chol liposomes did not form "vase structures". The internalization of DNA within "vases" is a unique feature of extruded DOTAP liposomes and have not been observed for any other DNA:liposome complex studied by cryo-electron microscopy (Frederik et al. (1991)). The "vase structures" observed for DOTAP:Chol may contribute to the high systemic delivery and gene expression achieved with these formulations.

Small Angle X-ray Scattering (SAXS)

DOTAP: Chol-DNA complexes were concentrated into a highly ordered structure by centrifugation or drying, and both techniques produced the same SAXS results. SAXS experiments were performed using a rotating anode x-ray source GX-13 (Elliot, England) focused by two bent x-ray mirrors. The 2-dimensional x-ray pictures were taken with a Franck-type camera at 15 cm distance from the sample, using Kodak phosphorous screens (Kodak, N.Y.) that were scanned by an image plate reader (PhosphorImager SI, Molecular Dynamics, CA). The radial intensity averages were determined using our modification of the NIH-Image 1.57 image processing program (Wayne Rasband, National Institutes of Health, MD). The results are shown in FIG. 8.

REFERENCES

Aksentijevich, I. et al. *Human Gene Ther.* 7, 1111 (1996).
Ashwell, G. and Harford, *J. Annu. Rev. Biochem.* 51, 531 (1982).
Blaese, R. M. *Scientific American* 6, 111 (1997).
Caplen, N. J. et al. *Nature Medicine* 1(1), 39–46 (1995).
Dragsten, P. R. et al. *Biochim. Biopys. Acta* 926, 270 (1987).
Felgner, J. H. et al. *J. Biol. Chem.* 269, 2550 (1994).
Felgner, P. L. et al. *Proc. Natl. Acad. Sci. USA* 84, 7413 (1987).
Felgner, P. L. *Hum. Gene Ther.* 7, 1791 (1996).
Felgner, P. L. *Scientific American* 6, 102 (1997).
Frederik, P. M. et al. *J. Microscopy* 161, 253 (1991).
Friedmann, T. *Scientific American* 6, 96 (1997).
Gao X. et al. *Biochem. Biophys. Res. Commun.* 179, 280 (1991).
Gustafsson, J. et al. *Biochim. Biophys. Acta* 1235, 305 (1995).
Hara, T. et al. *Gene Therapy* 2, 784 (1995).
Ho, D. Y. and Sapolsky, R. M. *Scientific American* 6, 116 (1997).
Hong, K. et al. *FEBS Lett.* 400, 233 (1997).
Kaneo, Y. et al. *Chem. Pharm. Bull.* 39, 999 (1991).
Lasic D. D. and Needham, D. *Chemical Reviews* 95, 2601 (1995).
Lasic D. D. et al. *J. Am. Chem. Soc.* 119, 832 (1997).
Lee, E. R. et al. *Hum. Gene Ther.* 7, 1701 (1996).
Liu, Y. et al. *J. Biol. Chem.* 270, 24864 (1995).
Liu, Y. et al. *Nature Biotech.* 15, 167 (1997).
Mislick, K. A. and Baldeschwieler, J. D. *Proc. Natl. Acad. Sci. USA* 93, 12349 (1996).
Murahashi, N. and Sasaki, A. *Biol. Pharm. Bull.* 19, 418 (1996).
Nabel, E. G., et al. *Science* 249, 1285 (1990).
Philip, R. et al. *J. Biol. Chem.*, 268, 16087 (1993).
Radler, J. O. et al. *Science* 275, 810 (1997).
Sambrook J. et al. *Molecular Cloning*, 2nd Edition, pp. 1.38–1.39 (1989).
Solodin, I. et al. *Biochemistry* 34, 13537 (1995).
Soriano P., et al. *Proc. Natl. Acad. Sci. USA* 80, 7128–7131 (1983).
Spanjer, H. H. and Scherphof, G. L. *Biochim. Biopys. Acta* 734, 40 (1983).
Spanjer, H. H. et al. *Biochim. Biopys. Acta* 774, 49 (1984).
Stamatatos, L. et al. *Biochemistry* 27, 3917 (1988).
Stribling R. et al. *Proc. Natl. Acad. Sci. USA* 89, 11277 (1992).
Thierry, A. R. et al. *Proc. Natl. Acad. Sci. USA* 92, 9742 (1995).
Tsukamoto, M. et al. *Nature Genetics* 9, 243 (1995).
Wang, C. et al. *Proc. Natl. Acad. Sci. USA* 84, 7851 (1987).
Wheeler, C. J. et al. *Proc. Natl. Acad. Sci. USA* 93, 11454 (1996).
Xu, Y. and Szoka, F. C. *Biochemistry* 35, 5616 (1996).
Zhu, N. et al. *Science* 261, 209 (1993).

We claim:

1. An invaginated vase-like liposome produced by the steps comprising:

i) heating 1,2-bis(olcoyloxy)-3-(trimethylammonio)-propane and at least one cholesterol or cholesterol derivative forming heated lipid components;

ii) hydrating said heated lipid components forming hydrated lipid components;

iii) sonicating said hydrated lipid components forming sonicated lipid components;

iv) extruding said sonicated lipid components sequentially through filters of decreasing pore size; and v) adding a biologically active agent to said extruded lipid components forming invaginated vase-like liposomes.

2. The liposome of claim 1, wherein the biologically active agent is DNA, thereby forming a DNA sandwich liposome.

3. The liposome according to claim 2 further comprising a targeting ligand to the exterior surface of said DNA-sandwich liposome.

4. The liposome according to claim 2 further comprising a second biologically active agent.

5. The liposome of claim 2 wherein the DNA, 1,2-bis(oleoyloxy)-3-(trimethylammonio)-propane and at least one cholesterol or cholesterol derivative carry a net charge value of 2.

6. A DNA-sandwich composite liposome comprising an invaginated vase-like structure having a plurality of lipid bilayers, and a DNA molecule positioned between two or more lipid bilayers of the sandwich liposome, having net charge of 2 and a size of 200–450 nm.

7. A method for preparing invaginated vase-like liposomes comprising the steps of:

i) heating a mixture of 1,2-bis(olcoyloxy)-3-(trimethylammonio)-propane and at least one of cholesterol or cholesterol derivative forming heated lipid components;

ii) hydrating said heated lipid components forming hydrated lipid components;

iii) sonicating said hydrated lipid components forming sonicated lipid components;

iv) extruding said sonicated lipid components sequentially through filters of decreasing pore size forming invaginated vase-like liposomes; and v) adding DNA to said invaginated vase-like liposomes forming DNA-sandwich liposomes.

* * * * *